(12) United States Patent
Sabharwal (10) Patent No.: US 11,357,421 B2
(45) Date of Patent: Jun. 14, 2022

(54) FORCED OSCILLATION TECHNIQUE BASED LUNG FUNCTION TESTING

(71) Applicant: Cognita Labs, LLC, Houston, TX (US)

(72) Inventor: Ashutosh Sabharwal, Houston, TX (US)

(*) Notice: Subject to any disclaimer, the term of this patent is extended or adjusted under 35 U.S.C. 154(b) by 653 days.

(21) Appl. No.: 16/075,369

(22) PCT Filed: Feb. 3, 2017

(86) PCT No.: PCT/US2017/016371
§ 371 (c)(1),
(2) Date: Aug. 3, 2018

(87) PCT Pub. No.: WO2017/136639
PCT Pub. Date: Aug. 10, 2017

(65) Prior Publication Data
US 2019/0046074 A1   Feb. 14, 2019

Related U.S. Application Data

(60) Provisional application No. 62/290,504, filed on Feb. 3, 2016.

(51) Int. Cl.
*A61B 5/085* (2006.01)
*A61B 5/00* (2006.01)
(Continued)

(52) U.S. Cl.
CPC .......... *A61B 5/085* (2013.01); *A61B 5/0002* (2013.01); *A61B 5/087* (2013.01); *A61B 5/097* (2013.01);
(Continued)

(58) Field of Classification Search
None
See application file for complete search history.

(56) References Cited

U.S. PATENT DOCUMENTS 4,326,416 A * 4/1982 Fredberg ............... A61B 5/085
600/533
4,333,476 A    6/1982 Downing, Jr.
(Continued)

FOREIGN PATENT DOCUMENTS

WO    2015005958 A1    1/2015

OTHER PUBLICATIONS

Badia, J. R.., et al. "Forced oscillation technique for the evaluation of severe sleep apnoea/hypopnoea syndrome: a pilot study." European Respiratory Journal 11.5 (1998): 1128-1134. (Year: 1998).*
(Continued)

*Primary Examiner* — Jacqueline Cheng
*Assistant Examiner* — Jairo H Portillo (57) ABSTRACT

An apparatus for patient's lung function testing using forced oscillation technique is described. The apparatus includes a sub-woofer configured to generate a pressure wave. The apparatus further includes a waveguide configured to direct the generated pressure wave to be introduced into airflow towards the patient's lung. The apparatus includes a pressure transducer configured to measure a change in pressure of the airflow and one or more flow transducers configured to measure a change in flowrate of the airflow, in response to the pressure wave introduced into the airflow. The apparatus includes a computing unit configured to determine a mechanical impedance of the patient's lung based on the measured change in pressure and flowrate of the airflow.

18 Claims, 8 Drawing Sheets

(51) Int. Cl.
*A61B 5/087* (2006.01)
*A61B 5/097* (2006.01)
*G01F 1/66* (2022.01)
*H04R 1/02* (2006.01)
*H04R 1/28* (2006.01)

(52) U.S. Cl.
CPC ............... *G01F 1/66* (2013.01); *H04R 1/028* (2013.01); *H04R 1/2857* (2013.01); *A61B 5/4842* (2013.01); *A61B 5/7425* (2013.01); *A61B 5/7475* (2013.01); *A61B 2560/0406* (2013.01); *A61B 2562/028* (2013.01); *A61B 2562/0247* (2013.01); *A61B 2562/043* (2013.01)

(56) References Cited

U.S. PATENT DOCUMENTS

| | | | | |
|---|---|---|---|---|
| 6,142,952 | A * | 11/2000 | Behbehani | A61B 5/085 600/484 |
| 2003/0067391 | A1 * | 4/2003 | Fitzgerald | G08B 21/0208 340/573.1 |
| 2006/0178592 | A1 * | 8/2006 | Nason | A61M 16/06 600/532 |
| 2009/0253994 | A1 | 10/2009 | Schuessler et al. | |
| 2010/0087751 | A1 * | 4/2010 | Warner | A61B 5/0051 600/559 |
| 2010/0147305 | A1 * | 6/2010 | Dellaca' | A61B 5/085 128/204.23 |
| 2011/0060237 | A1 | 3/2011 | Kurosawa et al. | |
| 2012/0289852 | A1 | 11/2012 | Van Den Aardweg | |
| 2013/0150747 | A1 | 6/2013 | Pompilio et al. | |
| 2015/0119743 | A1 | 4/2015 | Maksym et al. | |
| 2015/0128942 | A1 | 5/2015 | Tatkov et al. | |
| 2015/0283342 | A1 * | 10/2015 | Mielcarz | A61M 16/0078 128/202.22 |
| 2016/0007882 | A1 | 1/2016 | Bates | |
| 2016/0016020 | A1 | 1/2016 | Sieber | |

OTHER PUBLICATIONS

Farré, R., et al. "Servocontrolled generator to measure respiratory impedance from 0.25 to 26 Hz in ventilated patients at different PEEP levels." European Respiratory Journal 8.7 (1995): 1222-1227. (Year: 1995).*

Maes, Hannes, et al. "A fan-based, low-frequent, forced oscillation technique apparatus." IEEE Transactions on Instrumentation and Measurement 63.3 (2013): 603-611. (Year: 2013).*

Mori, V., et al. "Bandpass Speaker Box to Perform Forced Oscillation Technique Using the Wavetube Method." VI Latin American Congress on Biomedical Engineering CLAIB 2014, Paraná, Argentina 29, Oct. 30 & 31, 2014. Springer, Cham, 2015. (Year: 2015).*

* cited by examiner

FORCED OSCILLATION TECHNIQUE BASED LUNG FUNCTION TESTING

TECHNICAL FIELD

The present disclosure generally relates to a system and a method for a patient's lung function testing using forced oscillation technique, and more specifically relates to a portable apparatus for performing a patient's lung function testing using forced oscillation technique.

BACKGROUND

To diagnose lung-related ailments, e.g. Chronic Obstructive Pulmonary Disease (COPD) and asthma, lung function testing is often prescribed. Conventional methods of lung function testing provide measurements obtained during specific respiratory actions of the subject. For example, the most commonly used lung function test is spirometry. However, spirometry can be difficult to perform for some patients as it requires patient training to conduct an unnatural forced breathing maneuver for a successful test, and thus, is dependent on the patient's ability to conform. As a result, many important classes of patient population may not be able to properly use spirometry test. Such patient categories include children below the age of 6, older subjects, and mentally challenged or seriously ill patients who find it difficult to conform to standard procedures for the spirometry test. Furthermore, in many important health cases (e.g., cases with reversible obstruction), even if spirometry test can be successfully completed, it has shown to be ineffective in detecting and diagnosing many lung conditions. Thus, in those cases, spirometry is not an effective pre-screening or disease-tracking tool. Also, since spirometry requires an unnatural maneuver, a trained Pulmonary Function Testing (PFT) technician is essential. As a result, spirometry is often performed in PFT labs that can limit its easy accessibility in many cases, especially in resource-constrained environments.

Over the last few decades, several classes of lung function diagnostic procedures have been developed, which have been mainly useful for research purposes. Out of those, the class of techniques known as Forced Oscillation Technique (FOT) has shown the most promise as an alternative to spirometry. FOT addresses some of the major concerns with spirometry. In FOT-based tests, the patient simply breathes normally into a tube, and hence no active maneuver is required from the patient. As a result, unlike spirometry, the patient does not need to be trained, and hence no special technician is needed. For example, it has been successfully conducted in children as young as three years of age. Furthermore, FOT-based tests have shown to be highly predictive of many more lung conditions than spirometry. In some cases, it can diagnose COPD well in advance, compared to spirometry A challenge in reducing the size of the device for FOT-based testing is due to the requirement of very low frequencies of the input pressure waves. The FOT based tests use pressure waves in the frequency range of 5-50 Hz. The frequency of the pressure wave directly influences the size of the device used to generate the pressure wave. Smaller frequencies mean larger wavelengths, which implies that the size of the wave generator has to be correspondingly bigger. Furthermore, the amplitude of the measured signals due to the application of the pressure waves has to be large enough for the pressure and flow sensors to reliably measure the lung characteristics. To have strong signal strength, one needs strong input signal, and thus, in turn, we need a large aperture pressure wave generator to produce strong pressure waves.

WIPO Patent Application Number 2013163740A1 discloses a piezoelectric beam bending actuated device for measuring respiratory system impedance. The disclosed device is a piezoelectric material based forced oscillation system which uses a mesh to generate required forced pressure signals on the patient's airway system and pneumotach based flow sensors for measuring airflow. With the use of such components, the disclosed device may be able to achieve small size but may simultaneously require higher input power and have relatively high cost. Furthermore, such device may require system calibration before use in clinic settings due to the choice of signal generation means and sensor, which may be cumbersome.

Therefore, there is a need for a portable apparatus which can perform patient's lung function testing using forced oscillation technique and is relatively inexpensive compared to known devices.

SUMMARY

In one aspect, an apparatus for performing a patient's lung function testing using forced oscillation technique is described. The apparatus includes a housing. The apparatus further includes a mouthpiece attached to the housing and configured to allow the patient to inhale and exhale air therefrom. The apparatus includes a sub-woofer disposed within the housing and configured to generate a pressure wave. The apparatus further includes a waveguide coupled to the signal generator from one end and in fluid communication with the mouthpiece from another end in order to direct the generated pressure wave towards the mouthpiece to be introduced into airflow towards the patient's lung. The apparatus also includes a pressure transducer in fluid communication with the waveguide and configured to measure a change in pressure of the airflow in response to the pressure wave introduced into the airflow. The apparatus further includes one or more flow transducers associated with either one of the mouthpiece and the waveguide, and configured to measure a change in flowrate of the airflow in response to the pressure wave introduced into the airflow. The apparatus also includes a computing unit in signal communication with the pressure transducer and the one or more flow transducers. The computing unit is configured to determine a mechanical impedance of the patient's lung based on the measured change in pressure and flowrate of the airflow.

In another aspect, a system for patient's lung function testing using forced oscillation technique is described. The system includes a sub-woofer configured to generate pressures. The system further includes a waveguide configured to direct the generated pressure wave to be introduced into airflow towards the patient's lung. The system includes a pressure transducer configured to measure a change in pressure of the airflow in response to the pressure wave introduced into the airflow. The system also includes one or more flow transducers configured to measure a change in flowrate of the airflow in response to the pressure wave introduced into the airflow. The system includes a computing unit configured to determine a mechanical impedance of the patient's lung based on the measured change in pressure and flowrate of the airflow.

In yet another aspect, a method for patient's lung function testing using forced oscillation technique is described. The method includes generating, via a sub-woofer, pressure waves. The method further includes superimposing the generated pressure waves with airflow towards the patient's lung. The method further includes measuring, via a pressure transducer, a change in pressure of the airflow in response to the pressure wave introduced into the airflow. The method also includes measuring, via a flow transducer, a change in flowrate of the airflow in response to the pressure wave introduced into the airflow. The method further includes determining a mechanical impedance of the patient's lung based on the measured change in pressure and flowrate of the airflow.

The details of one or more implementations are set forth in the accompanying drawings and the description below. Other aspects, features, and advantages of the subject matter disclosed herein will be apparent from the description, the drawings, and the claims.

DETAILED DESCRIPTION

Illustrative embodiments of the present invention are described below. The following explanation provides specific details for a thorough understanding of and enabling description for these embodiments. One skilled in the art will understand that the invention may be practiced without such details. In some instances, well-known structures, processes and functions have not been shown or described in detail to avoid unnecessarily obscuring the description of the embodiments.

It shall be noted that unless the context clearly requires otherwise, throughout the description, the words "comprise," "comprising," "include," "including," and the like are to be construed in an inclusive sense as opposed to an exclusive or exhaustive sense; that is to say, in the sense of "including, but not limited to." Words using the singular or plural number also include the plural or singular number, respectively while adhering to the concepts of the present invention. Furthermore, references to "one embodiment" and "an embodiment" are not intended to be interpreted as excluding the existence of additional embodiments that also incorporate the recited features.

The details of the claimed invention will be explained in consideration of the following description read in conjunction with the appended figures.

Figure 1:
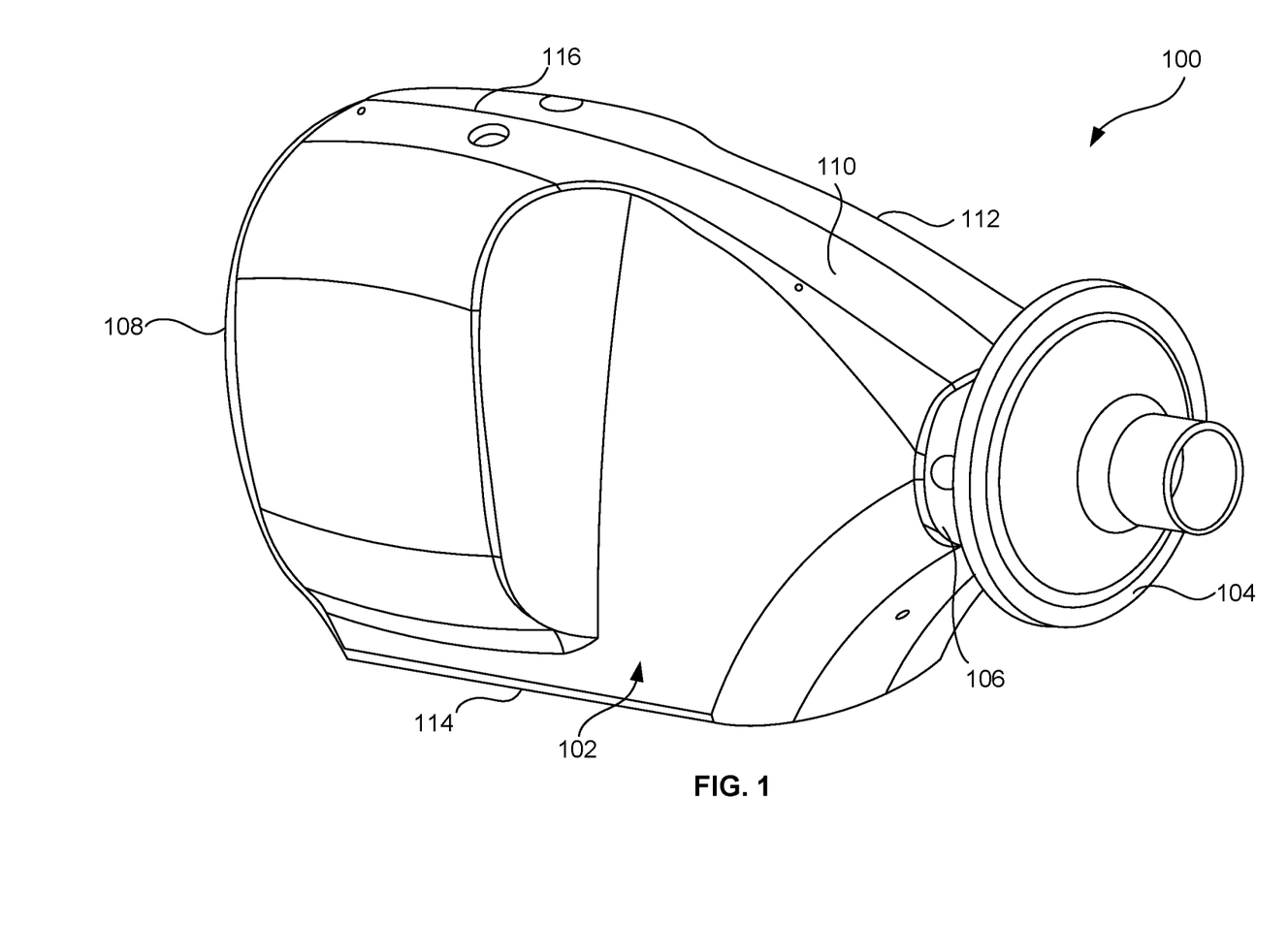
FIG. 1 illustrates a side perspective view of an apparatus for performing a patient's lung function testing using forced oscillation technique, in accordance with one or more embodiments of the present disclosure.

FIG. 1 illustrates a perspective side view of an apparatus, generally referenced by the numeral 100, according to one or more embodiments of the present invention. In the present embodiment, the apparatus 100 is a portable diagnostic device for performing a patient's lung testing function. In particular, the apparatus 100 is configured to determine a function of a patient's respiratory system. The function, as described herein, may be a mechanical parameter associated with the patient's lung. For example, the apparatus 100 is configured to determine an acoustic or mechanical impedance of the patient's lung for the purpose of diagnosing known respiratory diseases.

As illustrated in FIG. 1, the apparatus 100 includes a housing 102 in which various electronic components of the apparatus 100 are enclosed. In general, the housing 102 may be a rigid structure to properly enclose the various components and may further be able to withstand an accidental fall or the like. The housing 102 may be made of any suitable material, such as, but not limited to, plastic or some other light weight material. As may be seen, the housing 102 is symmetrically formed to accommodate both right or left handed operator use. In the illustrated example, the housing 102 has a substantially oblong or elliptical cross-sectional profile. It may be understood that the elliptical profile of the housing 102 facilitates the apparatus 100 being gripped in an operator's hand. However, in alternative examples, the housing 102 may have a non-elliptical cross-sectional profile without any limitations.

Further, as illustrated, the apparatus 100 includes a mouthpiece 104. The mouthpiece 104 may be attached to a front end 106 of the housing 102, opposite to the rear end 108. The mouthpiece 104 may allow the patient to inhale air therefrom. The mouthpiece 104 may be shaped to allow a patient to maintain an airtight seal of the lips around without much discomfort. In some examples, the mouthpiece 104 may allow to use a disposable filter (not shown) therewith. The disposable filter may be required to be replaced with each use of the apparatus 100 for testing of any patient. As may be understood, this may be required to prevent risk of any bacterial infection to the patient from multiple uses of the apparatus 100 by different patients.

Figure 2:
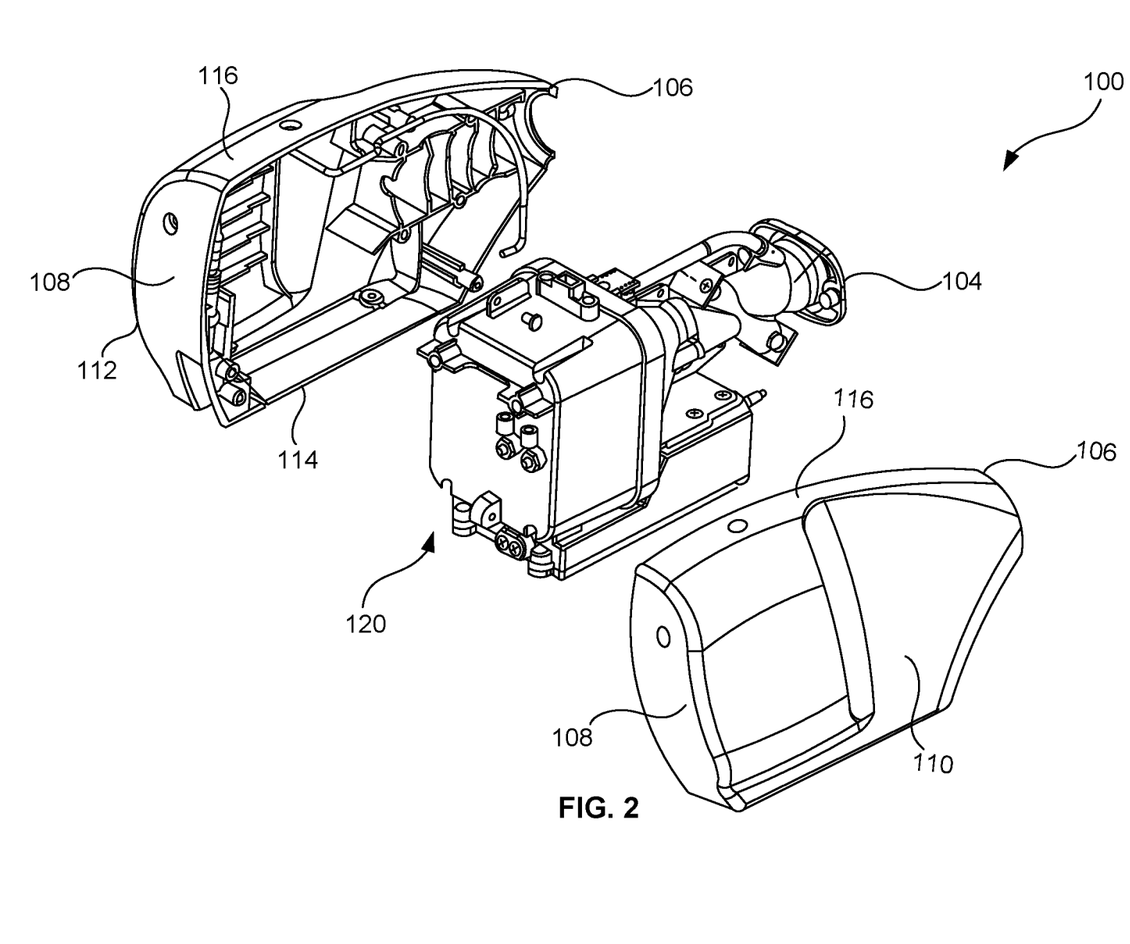
FIG. 2 illustrates an exploded view of the apparatus of FIG. 1, in accordance with one or more embodiments of the present disclosure.

FIG. 2 illustrates an exploded view of the apparatus 100, in accordance with one or more embodiments of the present disclosure. As illustrated, the housing 102, of the apparatus 100, is symmetrically-formed and includes a pair of opposed two sidewalls 110, 112. In the illustrated example, each sidewall 110 and 112 extends arcuately between the front end 106 and the rear end 108; and are connected together, such that a cavity is defined therebetween. For the purpose of illustration, the various fasteners, such as, but not limited to, nuts and bolts have not been shown in FIG. 2 to clearly show the selected components required for functioning of the apparatus 100.

Further, as illustrated in FIG. 2, a bottom surface 114 of the housing 102 is substantially planar, and extends substantially perpendicularly between the sidewalls 110, 112; and between the front end 106 and the rear end 108, respectively. Further, a top surface 116 of the housing 102 also extends between the sidewalls 110, 112; and extends obliquely between the front end 106 and the rear end 108 with respect to the bottom surface 114. It may be contemplated that the illustrated design of the housing 102 is exemplary only, and the housing 102 may have any other suitable shape and design without any limitations.

Figure 3:
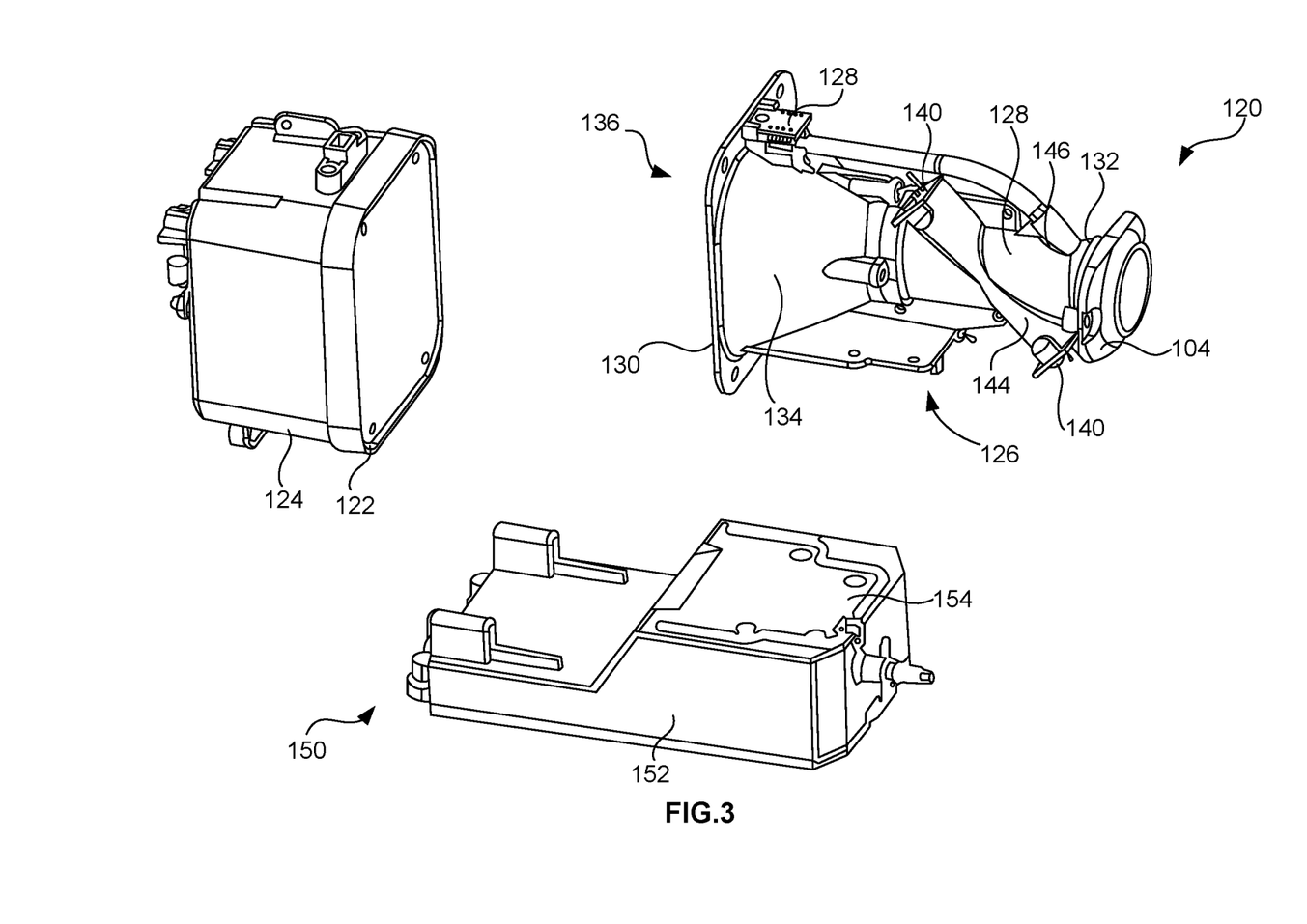
FIG. 3 illustrates an exploded view of functional components of the apparatus of FIG. 1, in accordance with one or more embodiments of the present disclosure.

FIG. 2 also shows a functional assembly 120 of the apparatus 100 which perform the requisite functions of lung testing therein. As may be contemplated by a person skilled in the art that various components of the functional assembly 120 may be joined together by using suitable types of fastening arrangements (not shown). FIG. 3 illustrates a detailed exploded view of the functional assembly 120 of FIG. 2 to separately and individually show the various components. These various components and their relationship with each other have been described below in view of FIG. 3.

As illustrated in FIG. 3, the apparatus 100 includes a signal generator 122. In an embodiment of the present disclosure, the signal generator 122 is a sub-woofer. Hereinafter, the terms "signal generator" and "sub-woofer" have been interchangeably used without any limitations. For the purpose of the present disclosure, the sub-woofer 122 may include a speaker, a woofer or any other device capable of generating pressure or acoustic waves. In examples of the present disclosure, the sub-woofer 122 includes a driver (not shown) having a diameter in the range of 2 to 5 inches. In a particular example, the apparatus 100 employs the sub-woofer 122 with a driver having a diameter of 3 inches. As may be seen, the sub-woofer 122 may be housed in a rectangular enclosure 124. It may be understood that the dimensions and shape of the enclosure 124 may conform to the corresponding shape and dimensions of the sub-woofer 122. The dimensions of the enclosure 124 are determined in a way to maximize power output at lowest frequency while keeping the volume of the enclosure 124 for portability. This is done via fine tuning the Q factor and resonant frequency of the driver and computing the minimum possible dimensions for the enclosure 124. Such design techniques are well known in the art and have not been described herein in detail for the brevity of the disclosure.

In an embodiment, the sub-woofer 122 is configured to generate pressure wave with a predefined frequency. To implement the pressure wave, the sub-woofer 122 employs a predefined waveform data that may be stored on an on-board flash memory (not shown) or the like. This data is then sampled by a microcontroller and sent to a digital-to-analog converter (DAC) chip (not shown). In most cases, a sampling rate of 4-8 KHz may suffice but the exact value may be determined based on the specific design of the sub-woofer 122. The predefined signal profiles, used to generate the pressure waves, may be replaced with different product versions with different speaker specifications. Furthermore, in different examples, the pressure waves may be flexibly changed using the wireless or wired link to a computing device that creates the signal in real-time, as will be explained later in detail. In most cases, the generated pressure wave is then fed to an amplifier. In the present example, a Class D amplifier may be an ideal choice for low-power application due to its power-efficient implementation.

In particular, the sub-woofer 122 may generate multiple pressure waves with discrete frequencies in a predefined frequency range. In one example, the predefined frequency range may be 3-50 Hz. The choice of frequency range or discrete frequency may vary from one application to another. For example, in one example, only one frequency may be used and in another example, multiple discrete frequencies are generated by the signal generator 122. In an embodiment, the power, number and frequency values may be configured by a software running either on the apparatus 100 itself or on a computing device associated with the apparatus 100 via a wireless or wired link; and the choice of the frequencies and their associated parameters (power and values) may be either manually configured by the operator or by the software automatically, according to the following equation, $$y = \sum_{i=1}^{N} A_i \sin(2\pi f_i t + \Phi_i)$$

where, $A_i$=coefficient; $f_i$=[3, 50] Hz; $\Phi_i$=phase delay

In an embodiment, the power of the sub-woofer 122 output and individual or discrete frequencies of the pressure waves may be dynamically changed by the computing device based on the computed coherence value, measured power output of the individual frequencies and maximum allowable pressure amplitude. In one example, the sub-woofer 122 is configured to dynamically generate the pressure waves with one or more of varying numbers of both power and frequency. The methods for calculation of such values may be contemplated by a person skilled in the art and thus have not been described in detail herein for the brevity of the disclosure. It may be understood that the power output values (or in other words, the output pressure values) is measured at the mouthpiece 104.

Further, as illustrated in FIG. 3, the apparatus 100 includes a connecting member 126 coupling the signal generator 122 to the front end 106 of the housing 102, proximal to the mouthpiece 104. In particular, the connecting member 126 includes a waveguide 128 which is coupled to the signal generator 122 from one end 130 and in fluid communication with the mouthpiece 104 from another end 132. In general, the waveguide 128 may be in the form of a channel or a tube to provide a laminar flow therein. The waveguide 128 allows to direct the pressure wave, generated by the signal generator 122, towards the mouthpiece 104, which may therefrom be introduced into the airflow towards the patient's respiratory system, when the patient inhales air via the mouthpiece 104.

In one embodiment, the waveguide 128 may be shaped resulting in minimal possible obstructions in the path of transmission of the pressure wave therein. In one example, the waveguide 128 has either one of circular, oval and rectangular cross-sectional shape. Further, as may be seen, due to the mismatch in the dimensions of the signal generator 122 and the waveguide 128; and therefore, they cannot be connected directly. In one example, the waveguide 128 may include a curved transition portion 134 which allows for smooth coupling of the waveguide 128 with the rectangular enclosure 124 of the signal generator 122, and thus helps with reducing the turbulence caused to the pressure waves when propagating therein. The mechanical design of the waveguide 128, including the shape, size and dimensions, is optimized to preserve the laminarity and reducing the dead-space for transmission of the pressure wave during the lung testing process.

Referring again to FIG. 3, the apparatus 100 includes a sensing unit 136 configured to measure pressure and flow-rate of the airflow therein. The sensing unit 136 may include multiple sensors to achieve the said purpose. In one embodiment, the sensing unit 136 includes a pressure transducer 138 in fluid communication with the waveguide 128. The pressure transducer 138 may be configured to measure a change in pressure of the airflow in response to the pressure wave introduced into the airflow. Further, the sensing unit 136 may include one or more flow transducers 140 associated with either one of the mouthpiece 104 and the waveguide 128. The flow transducers 140 are configured to measure a change in flowrate of the airflow in response to the pressure wave introduced into the airflow.

In one example, the pressure transducer 138 is a microelectromechanical system (MEMS) based transducer. Furthermore, the pressure transducer 138 is an ultra-low-power MEMS pressure transducer to measure pressure response of the patient's respiratory system to the externally applied pressure waves. In the present example, maximum peak-to-peak pressure generated by the range of sub-woofer 122 is about 300 N/m$^2$. Adding the mouth-pressure, the pressure transducer 138 may have specifications with measurement range of 0-900 N/m$^2$, and the measurement sensitivity may be increased via oversampling and averaging the data. In an embodiment, the apparatus 100 may employ a flexible pipe 142 which connects the pressure transducer 138 to an opening (not shown) in the waveguide 128. In one example, the said opening may be located proximal to the mouthpiece 104 in order to have appropriate signal-to-noise (SNR) ratio for pressure fluctuation measurement. Alternatively, the pressure transducer 138 may be coupled directly to the opening in the waveguide 128.

Figure 4:
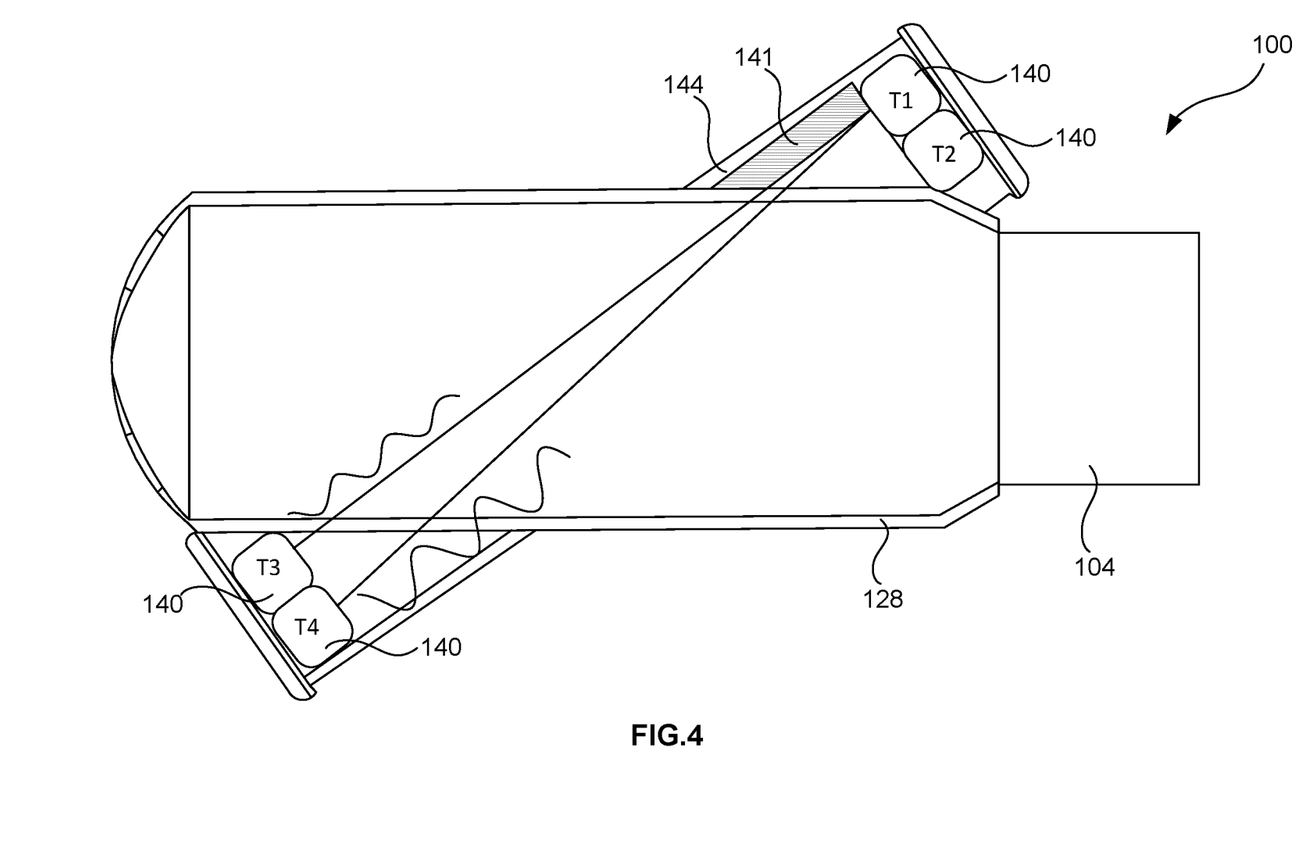
FIG. 4 illustrates a partial planar sectional view of the apparatus of FIG. 1, in accordance with one or more embodiments of the present disclosure.

Further, in an embodiment, the one or more flow transducers 140 are ultrasonic flowmeters. Hereinafter, the terms "flow transducer" and "ultrasonic flowmeter" have been interchangeably used without any limitations. The ultrasonic flowmeters 140 offer a non-invasive method of measuring airflow. As illustrated in FIG. 4, it may be understood that at least two such ultrasonic flowmeters 140 may be arranged radially opposite on the waveguide 128 for the purpose of measurement of flowrate of airflow therein. In ultrasonic flowrate measurement, an ultrasonic signal is transmitted in the direction of the airflow (downstream) and another ultrasonic signal is transmitted against the direction of the airflow (upstream). If there is no flow, time taken by the two signals is same in both directions. However, if flow is present then upstream and downstream signals are delayed by Δt. The differential time is then used as an indicator of the velocity or flowrate of the airflow.

In one embodiment, the one or more flow transducers 140 are positioned in an inner wall of the mouthpiece 104 or the waveguide 128, such that the one or more flow transducers 140 are disposed in direct contact with the airflow. For this purpose, the mouthpiece 104 and/or the waveguide 128 may have holes therein in which the flow transducers 140 may be engaged. Such design results in a stronger signal reception and has no reflections. In an alternate embodiment, as illustrated in FIG. 4, the one or more ultrasonic flowmeters 140 are positioned at an outer wall of the mouthpiece 104 and/or the waveguide 128. Although the suggested mechanical placement may result in relatively higher signal loss and hence lower SNR, and added reflections due to impedance mismatching, but the present design may overcome such limitations as described below.

Firstly, to compensate for the loss in signal, the present apparatus 100 may employ multiple pairs of flow transducers 140 to capture the same signal, as illustrated in FIG. 4. Since each flow transducers 140 captures a copy, possibly delayed version of the signal, the total energy captured by the array of the flow transducers 140 is larger than any single flow transducers. As an example, if these multiple signals are captured from three sensors and jointly processed, optimally for coherently addition, then the resulting sum signal may have a larger signal-to-noise ratio. The gain in SNR may be as large as $20 \log_{10}(M)$; where M is the number of flow transducers 140. An example computation with three sensors yields a gain of $20 \log_{10}(3)$ provides 9.5 dB of signal gain. Secondly, to reduce the reflections, a tight acoustic coupling is proposed between the flow transducers 140 and the walls of the mouthpiece 104 and/or the waveguide 128, through multi-layer physical case design. In the proposed design, a thin ultrasound gel (generally labeled as 141) filled air-pocket is established between the two materials with potentially very different acoustic impedance. The gel 141 may assist in transferring acoustic energy from flow transducer 140 to the walls of the mouthpiece 104 and/or the waveguide 128 and then from the radially opposite wall to the receiver end of flow transducer 140, without any substantial loss due to reflections of the signals.

In the embodiments of the present disclosure, the flow transducer 140 may need to measure minute flow fluctuations superimposed on normal breathing, via the mouthpiece 104. To provide sufficient signal quality to the short range of flow values, the resolution of the flow transducer 140 needs to be less than 10 milliliter/second. Therefore, to measure low flow-rate with closely placed flow transducers 140, the flow transducers 140 may need be able to capture very short transit-times. In the present example, the flow transducer 140 may need to measure transit-time with picosecond resolution. For this purpose, the electronic measurement clock may have to run at a few hundred MHz and the corresponding circuit may have to deploy a very high-speed microprocessor to analyze the data. In one example, a dedicated ASIC chipset is used to measure transit-times and forward the results to a low-power microcontroller. In addition, utility of the flow transducer 140 is to measure resulting fluctuations in the flow and not the underlying breathing signal like traditional respiratory medical flowmeters. Thus, higher sampling rate is needed to capture the high frequency component of the flow signal. In one example, the ultrasonic flowmeter 140 is configured to measure air flow with lowest flowrate of 5 mL/s and operate at with sampling rate greater than and equal to 500 Hz. For this purpose, the ultrasonic flowmeter 140 may be driven at higher than 100 kHz to facilitate higher flow sampling rate.

In one example, the apparatus 100 may include a mechanical tube 144 that creates a channel between the pair of flow transducers 140, as may be seen in FIG. 4. The tube 144 ensures that all the flow layers cross the beam created by the opposite flow transducers 140. This is important in order to measure small fluctuations in the flow created by the vibration of the sub-woofer 122. In order to reduce the resistance of the tube 144 itself and to allow maximum transport of the pressure wave to the mouthpiece 104, a width of the tube 144 is increased and thus imparting the tube 144 an oval or rectangular shape.

Further, in order to allow patients to breath in and out of the apparatus 100, a bias flow vent 146 may be provided on the wall of the waveguide 128. The size and location of the vent 146 may be carefully selected. The vent 146 needs to be large enough for the patients to easily breathe without difficulty but not too large to preserve the power of the pressure waves generated by the signal generator 122 inside the waveguide 128. In one example, multiple small vents 146 may be provided on the top side wall of the waveguide 128. This creates a mechanical filter that offers low resistance to low-frequency breathing flow but high resistance to the high-frequency components of breathing flow generated due to the imposed pressure waves, thus reducing the leakage of the generated pressure. That is, the vents 146 of varying size allow inhalation and exhalation of air by the patient, and block dust particles. Placement on the top side wall also make sure that patients do not accidently block the vent 146 by placing their hand. The vent 146 may be accompanied by a mesh (not shown) to prevent dust particles from entering. The mesh may aid with filtering function as described above.

Referring back to FIG. 3, the apparatus 100 may also include an electronic assembly 150. The electronic assembly 150 may enclose all the electronic components of the apparatus 100. In the illustration, the electronic assembly 150 has been shown to be located at a bottom portion of the housing 102; however, the electronic assembly 150 may alternatively be located in some other portion based the design constrains of the apparatus 100. The electronic assembly 150 may include a power source 152 such as a battery, which allows the apparatus 100 of the present disclosure to be used portably, making mobile applications of the apparatus 100 possible. The power source 152 may provide power to drive all the electronic components of the apparatus 100, including, the signal generator 122 and the corresponding amplifier, the pressure transducer 138 and the flow transducers 140 in the sensing unit 136, etc. In some examples, a step-up power converter (not shown) generating high voltage may optionally be employed for driving ultrasonic flowmeters 140 from the portable power source 152.

Further, the electronic assembly 150 may also include a computing unit 154 (generally labelled in FIG. 3) disposed in signal communication with the pressure transducer 138 and the one or more flow transducers 140. In one example, the computing unit 154 may be located within the housing 102. In another example, the computing unit 154 may be located partially within the housing 102 and partially remote to the housing 102, as will be discussed later. The pressure and flow values are communicated to the computing unit 154 via wireless/wired communication channel. After capturing flow and pressure waves, calibration and high-pass filtering may be applied to extract resultant pressure and flow fluctuations from the base breathing signal. After extraction is done, the computing unit 154 may employ empirical or Welch estimation (or another alternate suitable estimation method), as may be contemplated by a person skilled in the art. The computing unit 154 is configured to determine a mechanical impedance of the patient's respiratory system based on the measured change in pressure and flowrate of the airflow, as will be discussed later in more detail.

At different frequencies, the computing unit 154 may also calculate coherence function to check the validity of the result. The equations for calculation of the coherence function is well known and have not been described herein for the brevity of the disclosure. If desired coherence value is not achieved, the computing unit 154 may alter the power of the transmitted pressure wave or increase the length of the test in order to increase the signal quality and coherence value. In some examples, the same computing unit 154 may also generate raw signals for the sub-woofer 122 to generate pressure waves. In some examples, the computing unit 154 may be remote to the housing 102 and may connect to the sensing unit 136 over some wired or wireless communication channel, such as, but not limited to, Bluetooth, Wi-Fi, USB cable to collect raw pressure and flow values.

Figure 6:
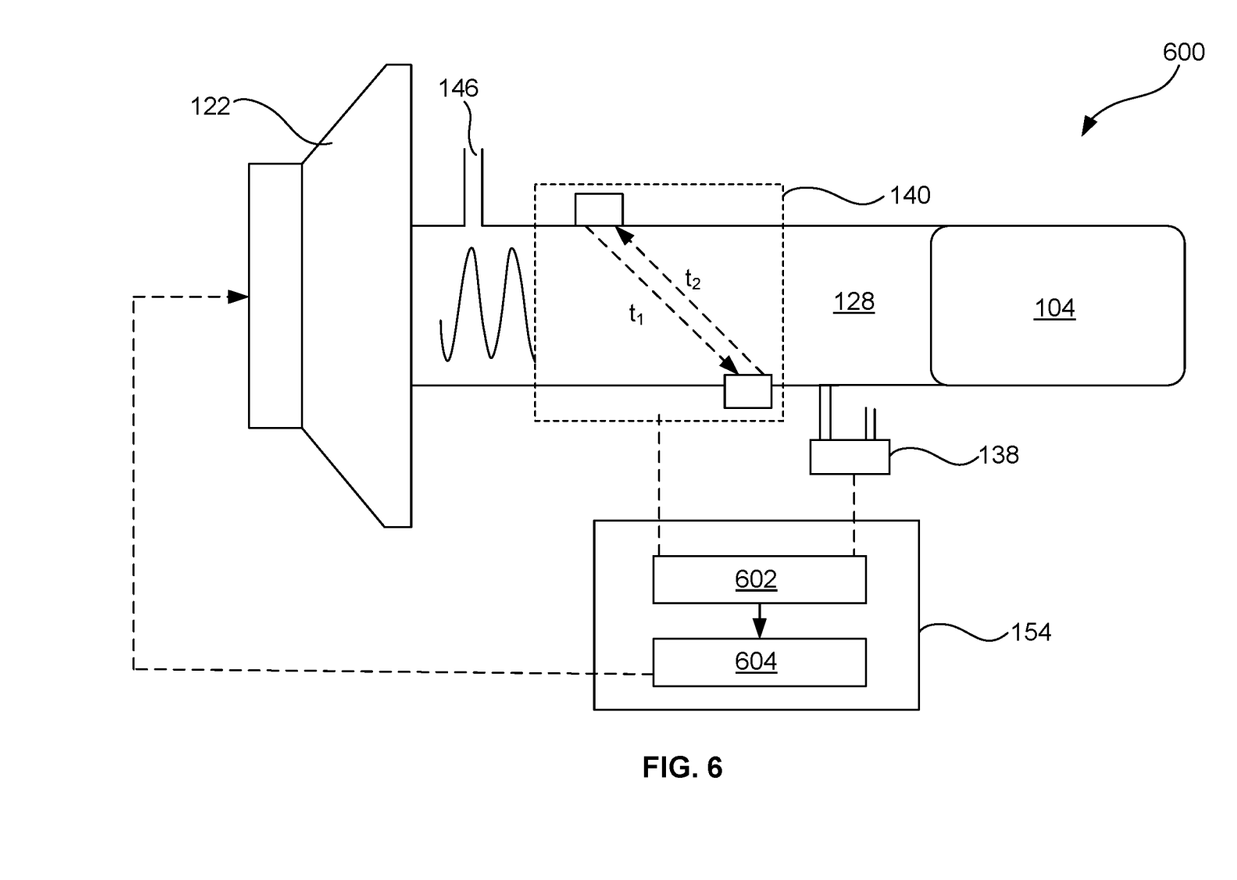
FIG. 6 illustrates a schematic diagram of a system for the patient's lung function testing using forced oscillation technique, in accordance with one or more embodiments of the present disclosure.

The present disclosure further provides a system 600, as schematically illustrated in FIG. 6, for patient's lung function testing using forced oscillation technique. In general, the system 600 may incorporate the apparatus 100 for achieving the said purpose. That is, the system 600 may include the sub-woofer 122 to generate the pressure wave. The system 600 may also include the waveguide 128 to direct the generated pressure wave to be introduced into airflow towards the patient's lung. The system 600 may further include the pressure transducer 138 to measure a change in pressure of the airflow in response to the pressure wave introduced into the airflow and one or more flow transducers 140 to measure a change in flowrate of the airflow in response to the pressure wave introduced into the airflow. The computing unit 154, in the system 600, determines the mechanical impedance of the patient's lung based on the measured change in pressure and flowrate of the airflow.

In an embodiment, the computing unit 154, in the system 600, may include a transmitter 602 configured to transmit signals indicative of the measured change in the change in pressure and flowrate of the airflow; and a mobile device 604 in signal communication with the transmitter 602 to receive the signals indicative of the measured change in the change in pressure and flowrate of the airflow. The transmitter 602 may utilize any known transmission standard, such as, but not limited to, Bluetooth, Wi-Fi, GPRS, etc. Further, the mobile device 604, of the computing unit 154, configured to perform signal processing to calculate the mechanical impedance of the patient's lung based on the measured change in pressure and flowrate of the airflow. In terms of the apparatus 100, the transmitter 602 may be located within the housing 102 and the mobile device 604 may be located remote to the housing 102.

Figure 8:
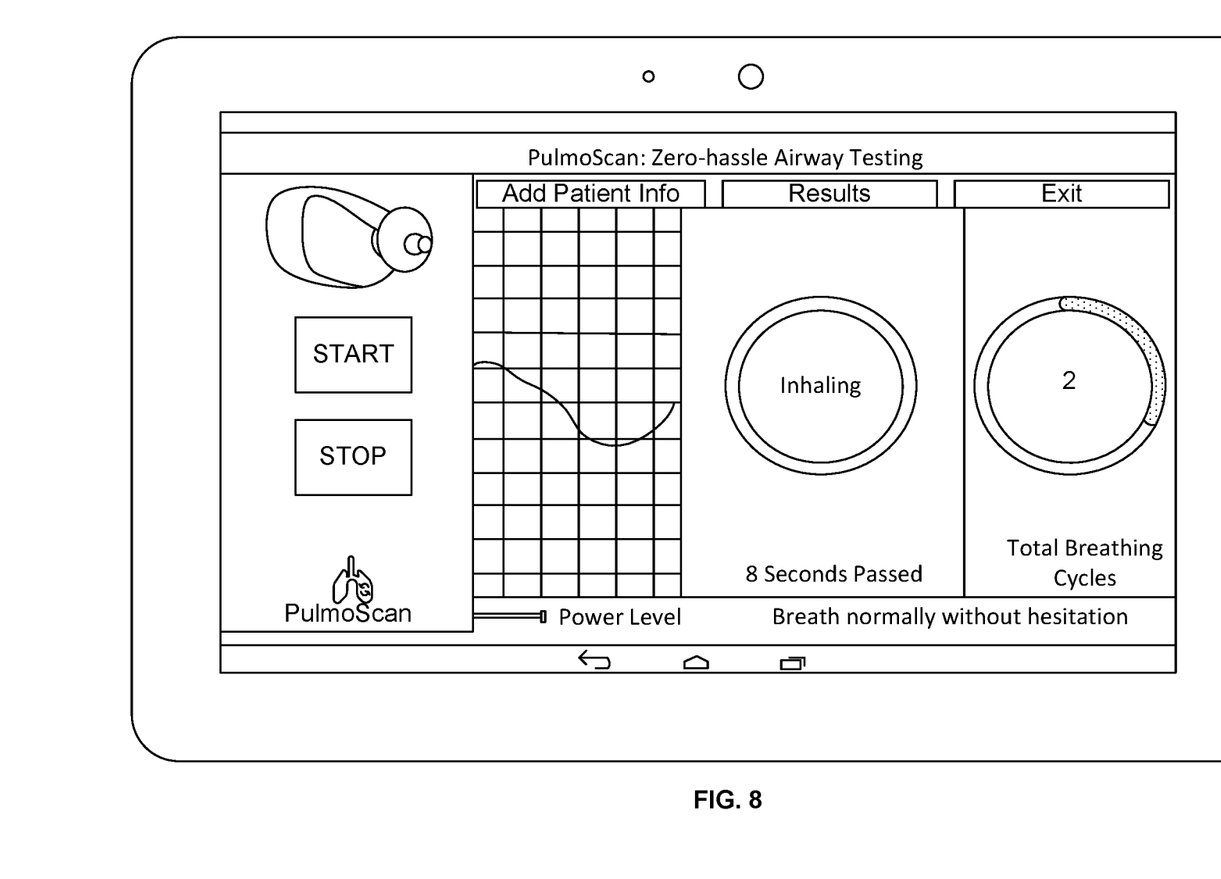
FIG. 8 illustrates an exemplary user interface, in accordance with one or more embodiments of the present disclosure.

In some examples, the mobile device 604 may further be configured to display the calculated impedance values on a display thereof. The mobile device 604 provides a user interface 606 to display the calculated impedance values in a predefined manner, e.g. both tabular and plot formats. FIG. 8 illustrates an exemplary embodiment of the user interface 606. In the present example, the mobile device 604 may be a portable and low-cost device. The mobile device 604 may be used to display real-time test information to clinical staff and/or patient, such as, but not limited to, breathing flow-time graph after low-pass filtering, time elapsed and number of breathing cycles by the patient. The mobile device 604 provides a patient management component which allows the staff to add new patients and conduct test sessions. Further, in some examples, the mobile device may also transmit the resulting values to the network connected EHR or private portal for remote storage and analysis. The cloud component syncs the data to the HIPAA compliant online portal for remote analysis.

In one embodiment, the mobile device 604 may also implement an audio-visual user feedback in order to minimize user/patient errors. During the FOT based lung testing, a minimum level of patient co-operation is required to ensure accurate results. Events such as coughing and hesitation are required to be detected and corrected by repeating the test. The mobile device 604 implements signal analysis algorithm that may detect phenomenon like coughing and hesitation by breath holding in real-time, and may selectively and automatically repeat that part of the test. Errors may be detected via one or more of checking tidal volume of the breathing cycle, frequency of the breathing cycle and coherence value of the calculated impedance of the breathing cycle. An audio-visual feedback unit of the mobile device 604 also reminds patients to remember to hold cheeks which is critical step to ensure impedance is not affected by the vibration of cheek walls, to make an air-tight seal around the mouthpiece 104 and keep the tongue position fixed. Such reminders may be given throughout the test using userfriendly audio and/or visual messages, and can also be combined with visual animations.

INDUSTRIAL APPLICABILITY

The present disclosure provides for estimating a patient's lung function, and specifically the characteristics of flow of air through lungs. To estimate air flow through lungs, Forced Oscillation Technique (FOT) is employed. In FOT, pressure (acoustic) signals are transmitted into the patient's lungs via their mouth and a response to the impinging waves is measured. Unlike conventional spirometry technique, the patient is required to provide only passive cooperation, by maintaining an airtight seal of the lips around the mouthpiece of the device, and breathing normally through the mouthpiece with a nose-clip occluding the nares.

Figure 5:
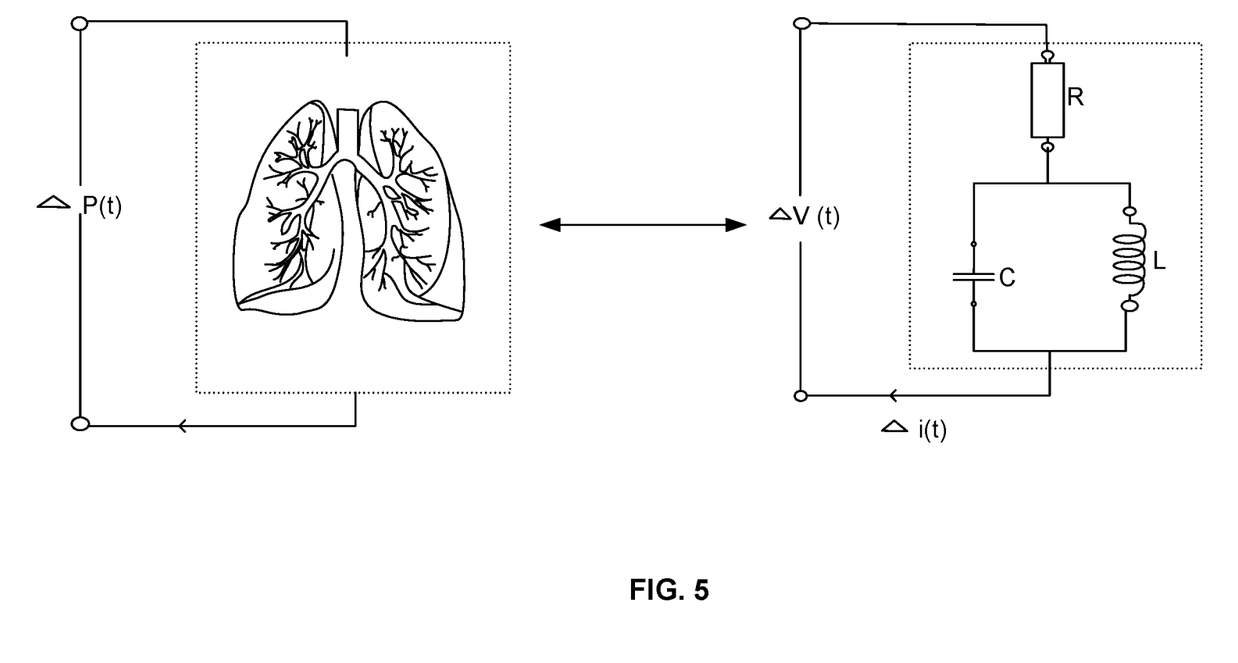
FIG. 5 illustrates schematic diagrams showing the analogy between an acoustic system with the patient's lung and an electrical system, in accordance with one or more embodiments of the present disclosure.

In an FOT system, measuring lung function is equivalent to measuring acoustic impedance of the lungs, and is performed by measuring the characteristics of the reflected pressure waves. The acoustic system has a direct analogy with an electrical system, conceptually depicted in FIG. 5. The flow in the pressure wave system is equivalent to current in the electrical system, and analogously pressure is equivalent to voltage. With this analogous representation, measuring acoustic impedance is equivalent to measuring electrical impedance of the lungs. As depicted in FIG. 5, impedance (acoustic or electrical) has three components, resistive, capacitive and inductive. In the context of lungs, resistive component represents opposition by the respiratory system to the airflow. Inductive component is due to the mass of air already present, and the capacitive component may be explained by elastic properties of the airways and the lung.

As may be known, to measure impedance in an electrical system, a known voltage of a specific frequency is introduced and the resulting current is measured. Different oscillation frequencies, ranging from 5 to 50 Hz, distinguish between large and small airways. Pressure waves of frequencies lower than 15 Hz travel deep into the lungs, while frequencies higher than 20 Hz reach intermediate size airways. Thus, low frequency response reflects small airway impedance and high frequency response characterizes large airways. The impedance is a complex ratio (both real and imaginary components) of the voltage to the current in an alternating current circuit. Leveraging the analogy between electrical and acoustic system, acoustic impedance, Z(f) may be similarly measured by sending pressure waves of different frequencies, P(f) and measuring flow, V(f), for each incident pressure wave as:

$$Z(f) = \frac{P(f)}{V(f)}, f \in [5, 50].$$

A challenge in reducing the size of the device for FOT-based testing is due to the requirement of very low frequencies of the input pressure waves. The FOT based tests use pressure waves in the frequency range of 5-50 Hz. The frequency of the pressure wave directly influences the size of the device used to generate the pressure wave. Smaller frequencies mean larger wavelengths, which implies that the size of the wave generator has to be correspondingly bigger. Furthermore, amplitude of the measured signals due to the application of the pressure waves has to be large enough for the pressure and flow sensors to reliably measure the lung characteristics. To have strong signal strength, one needs strong input signal and thus in turn, we need a large aperture pressure wave generator to produce strong pressure waves.

Figure 7:
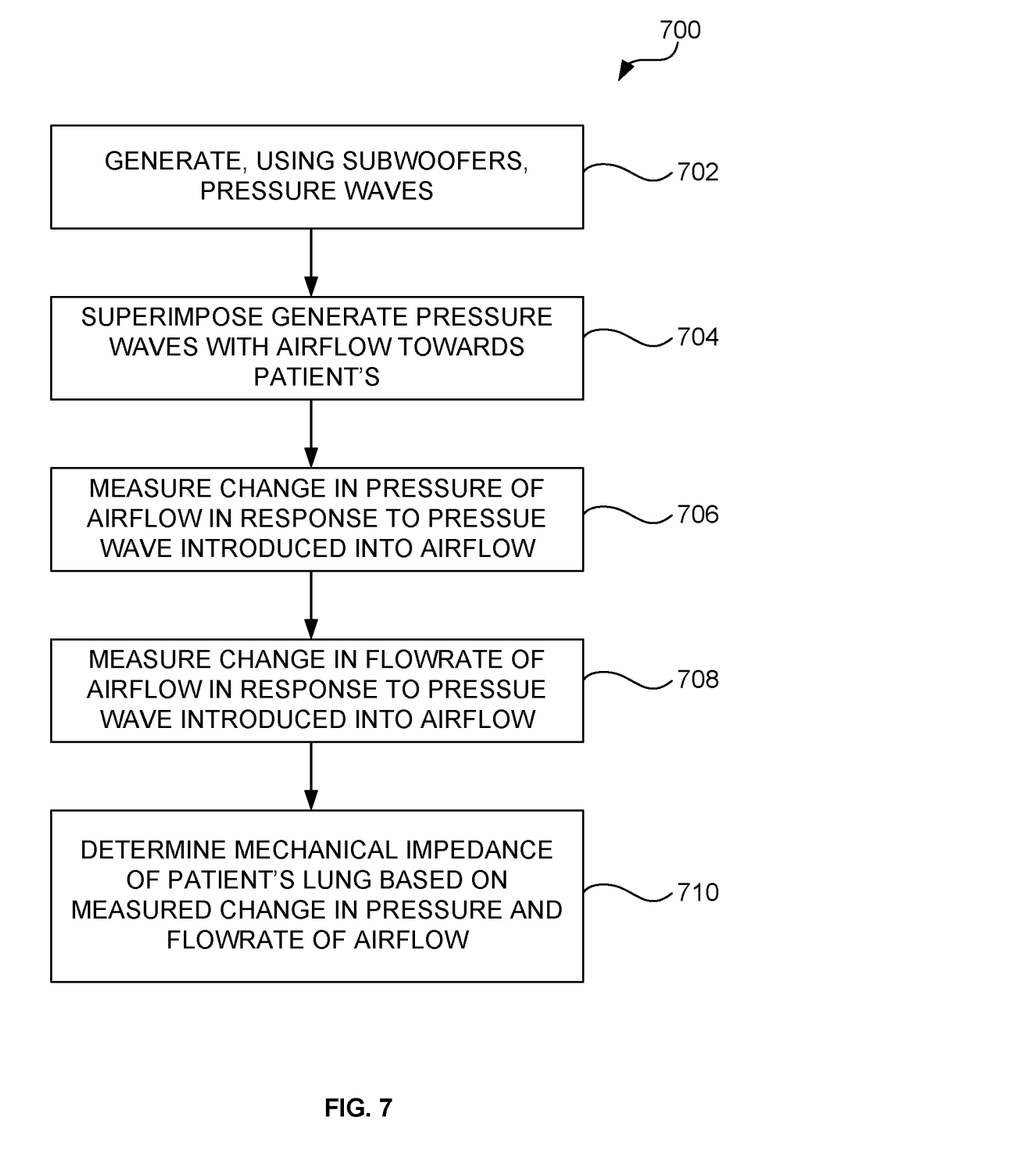
FIG. 7 illustrates a flow chart depicting the steps involved in a method for the patient's lung function testing using forced oscillation technique, in accordance with one or more embodiments of the present disclosure.

The present disclosure provides a method 700 for patient's lung function testing using forced oscillation technique, illustrated in the form of a flowchart in FIG. 7. At block 702, the method 700 includes generating, via the sub-woofer 122, pressure waves. At block 704, the method 700 includes superimposing the generated pressure waves with airflow towards the patient's lung. At block 706, the method 700 includes measuring, via the pressure transducer 138, a change in pressure of the airflow in response to the pressure wave introduced into the airflow. At block 708, the method 700 includes measuring, via the one or more flow transducers 140, a change in flowrate of the airflow in response to the pressure wave introduced into the airflow. At block 710, the method 700 includes determining a mechanical impedance of the patient's lung based on the measured change in pressure and flowrate of the airflow.

To overcome the above limitations and to achieve small size and low-power consumption of the lung function testing device, the apparatus 100 and the system 600 of the present disclosure employs some innovative techniques. The apparatus 100 of the present disclosure utilizes small-size sub-woofer 122 to generate the pressure waves. It may be understood that sub-woofers are often not designed to maximize their energy output in the desired range of 5-50 Hz; and as a result, their overall power in 5-50 Hz band is generally low. It may be known that in a small speaker system, the reduced area of the vibration coil limits the output power of the pressure oscillations and results in poor frequency response over lower frequencies. To compensate for the non-linear frequency response of the sub-woofers, the sub-woofer 122 of the present disclosure may be configured to provide different amount of power to individual frequencies and achieve flat frequency response.

Further, to counter the disadvantages of the reduced size of the sub-woofer 122, the apparatus 100 provides mechanical design of the waveguide 128 to maximize the energy transfer from the sub-woofer 122 to the mouthpiece 104. The present mechanical design of the waveguide 128 is important, since the small sub-woofer 122 generates low power pressure waves in frequencies of interest, and hence any loss due to mechanical design may reduce the overall test accuracy.

Traditional FOT devices add obstruction in the path in form of mesh which is used create a pressure differential and measure flow. In the present design, no such mesh or other obstruction is added in the waveguide 128 between the sub-woofer 122 and the mouthpiece 104, thereby allowing the use of small sub-woofers 122 and thus reducing the overall size of the apparatus 100. That is, in the present design, the measurement of flow and pressure is done without placing any sensors in the path of the pressure waves. In addition, the mechanical design of the waveguide 128 ensures laminar flow without increasing resistance offered to the pressure waves.

Further, in the present design, the use of ultrasonic flowmeters 140 offer a non-invasive method of measuring airflow. In addition, ultrasonic flowmeters are relatively small and may be placed outside the waveguide 128, making them a good choice for our space constrained application. The utilization of highly accurate ultrasonic flowmeters 140 combined with optimized placement also helps with reducing overall size of the apparatus 100 by being able to sense fluctuation in response to low power signals generated by the relatively small sub-woofers 122. Furthermore, the specialized oval/rectangular design of the tube 144 ensures laminar flow, and thereby high SNR for the flow transducer 140 while keeping low resistance to pressure waves. Also, by employing multiple flow transducers 140 in appropriate locations, the small time and phase differences may be translated into flowrate, by using signal processing algorithms operating on the signals measured by the sensors; thereby allowing the use of small sub-woofers 122.

Because of its cost and size advantage, the apparatus 100 of the present disclosure may be implemented as a diagnostic device or monitor in health care centers, at home or remotely by a telemedicine system. The light weight and inexpensive cost of the apparatus 100 make this device a major breakthrough to measurement of lung health in such diseases as asthma and chronic obstructive pulmonary disease (COPD). The apparatus 100 may be embodied in a diagnostic handheld device or as an attachment to the breathing circuit of an anesthesia machine or a mechanical ventilator.

The terms and descriptions used herein are set forth by way of illustrations only and are not meant as limitations. Examples and limitations disclosed herein are intended to be not limiting in any manner, and modifications may be made without departing from the spirit of the present disclosure as defined in the appended claims. Those skilled in the art will recognize that many variations are possible within the spirit and scope of the invention as defined in the following claims, and their equivalents, in which all terms are to be understood in their broadest possible sense unless otherwise indicated.

I claim:

1. An apparatus for performing a patient's lung function testing using forced oscillation technique, the apparatus comprising:
    a housing;
    a mouthpiece attached to the housing, wherein the mouthpiece is configured to allow the patient to inhale and exhale air therefrom;
    a sub-woofer disposed within the housing and configured to:
        generate multiple discrete pressure waves of different frequencies; and
        provide a different amount of power to each individual frequency of the multiple discrete pressure waves;
    a waveguide coupled to the sub-woofer from one end and in fluid communication with the mouthpiece from another end, and configured to direct the generated pressure waves toward the mouthpiece to be introduced into airflow towards the patient's lung;
    a pressure transducer in fluid communication with the waveguide and configured to measure a change in pressure of the airflow in response to the pressure waves introduced into the airflow;
    one or more flow transducers associated with either one of the mouthpiece and the waveguide, and configured to measure a change in flowrate of the airflow in response to the pressure waves introduced into the airflow; and
    a circuitry in signal communication with the pressure transducer and the one or more flow transducers, the circuitry configured to determine a mechanical impedance of the patient's lung based on the measured change in pressure and flowrate of the airflow.

2. The apparatus as claimed in claim 1, wherein the sub-woofer comprises a driver with diameter in the range of 2 to 5 inches.

3. The apparatus as claimed in claim 1, wherein the sub-woofer is further configured to generate the multiple discrete pressure waves within a predefined frequency range of 3-50 Hz.

4. The apparatus as claimed in claim 1, wherein the waveguide has either one of circular, rectangular and oval cross-sectional shape.

5. The apparatus as claimed in claim 4, wherein the waveguide comprises a curved transition portion to allow smooth coupling with a signal generator.

6. The apparatus as claimed in claim 1, wherein the waveguide comprises multiple vents of varying size to allow inhalation and exhalation, and block dust particles.

7. The apparatus as claimed in claim 1, wherein the pressure transducer comprises a microelectromechanical system based transducer.

8. The apparatus as claimed in claim 7, wherein the ultrasonic flowmeter is configured to measure airflow with lowest flowrate of 5 mL/s and operate at a sampling rate greater than and equal to 500 Hz.

9. The apparatus as claimed in claim 1, wherein the each of the one or more flow transducers comprises an ultrasonic flowmeter.

10. The apparatus as claimed in claim 1, wherein the one or more flow transducers are positioned in an inner wall of either one of the waveguide and the mouthpiece, such that the one or more flow transducers are disposed in direct contact with the airflow.

11. The apparatus as claimed in claim 1, wherein the one or more flow transducers are positioned at an outer wall of either one of the waveguide and the mouthpiece.

12. The apparatus as claimed in claim 1, wherein the circuitry comprises:
    a transmitter located within the housing and configured to transmit signals indicative of the measured change in pressure and flowrate of the airflow; and
    a mobile device remote to the housing and in signal communication with the transmitter to receive the signals indicative of the measured change in pressure and flowrate of the airflow, the mobile device configured to calculate the mechanical impedance of the patient's lung based on the measured change in pressure and flowrate of the airflow.

13. A system for patient's lung function testing using forced oscillation technique, the system comprising:
    a sub-woofer configured to:
        generate multiple discrete pressure waves of different frequencies; and
        provide a different amount of power to each individual frequency of the multiple discrete pressure waves;
    a waveguide configured to direct the generated pressure waves to be introduced into airflow towards the patient's lung;
    a pressure transducer configured to measure a change in pressure of the airflow in response to the pressure waves introduced into the airflow;
    one or more flow transducers configured to measure a change in flowrate of the airflow in response to the pressure waves introduced into the airflow; and
    a circuitry configured to determine a mechanical impedance of the patient's lung based on the measured change in pressure and flowrate of the airflow.

14. The system as claimed in claim 13, wherein the circuitry comprises a mobile device, the mobile device provides a user-interface to display data associated with the determined mechanical impedance of the patient's lung in a predefined manner.

15. The system as claimed in claim 13, wherein the circuitry is further configured to validate data associated with the measured change in pressure and flowrate of the airflow based on one or more of checking tidal volume of breathing cycle, frequency of the breathing cycle and coherence value of the calculated impedance of the breathing cycle.

16. A method for patient's lung function testing using forced oscillation technique, the method comprising:

generating, via a sub-woofer, multiple discrete pressure waves of different frequencies;

providing, via the sub-woofer, a different amount of power to each individual frequency of the multiple discrete pressure waves;

superimposing the generated pressure waves with airflow towards the patient's lung;

measuring, via a pressure transducer, a change in pressure of the airflow in response to the pressure waves introduced into the airflow;

measuring, via one or more flow transducers, a change in flowrate of the airflow in response to the pressure waves introduced into the airflow; and determining a mechanical impedance of the patient's lung based on the measured change in pressure and flowrate of the airflow.

17. The method as claimed in claim 16, wherein the multiple pressure waves are generated with discrete frequencies in a predefined frequency range of 3-50 Hz.

18. The method as claimed in claim 16, wherein the pressure transducer comprises a microelectromechanical system based transducer, and wherein the flow transducer comprises an ultrasonic flowmeter.

* * * * *